United States Patent
Lee

(10) Patent No.: US 6,423,053 B1
(45) Date of Patent: Jul. 23, 2002

(54) RELEASABLE TUBE ASSEMBLY

(76) Inventor: Han-Pin Lee, 6F-2, No. 36, Tung Hsin East Street, Taichung (TW)

( * ) Notice: Subject to any disclaimer, the term of this patent is extended or adjusted under 35 U.S.C. 154(b) by 0 days.

(21) Appl. No.: 09/482,475

(22) Filed: Jan. 12, 2000

(51) Int. Cl.⁷ .............................................. A61M 25/16
(52) U.S. Cl. ........................ 604/533; 604/523; 604/905
(58) Field of Search ................................. 604/533, 411, 604/415, 523, 195, 905, 240

(56) References Cited

U.S. PATENT DOCUMENTS

| | | | | |
|---|---|---|---|---|
| 5,071,413 A | * | 12/1991 | Utterberg .................... | 604/283 |
| 5,810,792 A | * | 9/1998 | Fangrow, Jr. et al. ....... | 604/533 |
| 5,976,115 A | * | 11/1999 | Parris et al. ................ | 604/283 |
| 6,096,011 A | * | 8/2000 | Trombley, III et al. ..... | 604/256 |
| 6,183,464 B1 | * | 2/2001 | Sharp et al. ................ | 604/533 |

* cited by examiner

Primary Examiner—Sharon Kennedy
Assistant Examiner—Kevin C. Sirmons
(74) Attorney, Agent, or Firm—Senniger Powers Leavitt and Roedel

(57) ABSTRACT

A releasable tube assembly, comprising: a male tube having a male tube body and a pair of opposing arms, in which the male tube body has an outer surface and a coupling end, and each of the arms includes: an attachment section, coupled to the outer surface of the male tube body; an intermediate angled section, extending upward from the attachment section; and a handle section, extending upward from said angled section, in which the intermediate angled section and the handle section are in non-contact with the outer surface of the male tube body; a female tube including: a female tube body having a connecting end which is tightly fitted with the coupling end of the male tube body; and a receiving chamber which connects to the connecting end of and communicates to the female tube body, in which the receiving chamber has an upper opening and two diametrically protruding hollow side wings to form a dimension which accommodates the intermediate angled sections of the opposing arms coupled to the male tube body, and the upper opening of the receiving chamber is provided with an inner flange for preventing the angled sections of the arms from leaving the receiving chamber.

8 Claims, 4 Drawing Sheets

RELEASABLE TUBE ASSEMBLY

FIELD OF THE INVENTION

The present invention relates to a releasable tube assembly which is primarily used in medical instruments to prevent accidental disconnection and leakage.

BACKGROUND OF THE INVENTION

Conventional connection methods for an administration set of infusion therapy, nasogastric or nasoduodenal tubes, blood tubing set of hemodialysis, delivery tubing set of peritoneal dialysis, breathing circuit of ventilator, urinary catheters et al. can be classified as follows:

a. Direct hub-to-hub connection: as shown in FIG. 5, a slip tip of a catheter is provided with outer protrusions and is directly inserted into the hub of the other catheter. To remove the tip from the hub, a user just slightly rotates the tip and pulls the tip away from the hub. The connection may cause leaks after long use. Also, unintended disconnection may occur by the movement of the patients.

b. Luer lock connection: an end of a catheter has a threaded lip for screwing into the hub of the other catheter. This requires time to secure the lip to the hub and blood may leak from the catheters.

c. Slip Luer connection: this connection combines the direct hub-to-hub connection and Luer lock connection. A user first makes the direct hub-to-hub connection and then screws the threaded lip into the hub of the other catheter. Similarly, it takes a little time to secure the lip to the hub. Further, it may be disconnected by incomplete connector insertion or Luer lip securing and thus results in air or blood leakage.

d. Simple male and female connection: as shown in FIG. 6, the tip of a catheter is positioned within a blood vessel, and a tapered male end of a three-way connector is inserted into a tapered female end of the catheter and is retained therein by friction therebetween. However, due to their poor locking mechanisms, this makes them a prime candidate for being accidental knocked off at a later time.

e. Saf-T-Clik connection: as shown in FIG. 7, a small L-shaped groove is formed on the side wall near the end of a catheter with a larger diameter. A small knob is provided on the side wall near an end of the other catheter with a smaller diameter. By inserting the end of the catheter into the end of the other catheter and inserting the knob into the groove and turning the knob until a "click" sound is heard, these two catheters can be connected and locked. It takes more time to connect the catheters until a "click" sound occurs. The connection is not complete if the knob is not entirely inserted into the groove.

By using any one method of the connections indicated above, disconnection between the catheters can occur easily. In the case of higher pressure ventilation or infusion pump therapy, the pressure can cause disconnection and leakage. Because of the above reasons, medical care professionals need a simple and effective means to secure the tubings, catheters or circuits.

SUMMARY OF THE INVENTION

To overcome the above drawbacks, it is an objective of the present invention to provide a releasable tube assembly wherein the secure connection and the sealing of the ends of tubes, particularly medical tubings, catheters or circuits, can be obtained.

It is another objective of the present invention to provide a releasable tube assembly wherein no leakage occurs.

It is another objective of the present invention to provide a releasable tube assembly wherein accidental disconnection between two tubes can be prevented.

It is a further objective of the present invention to provide a releasable tube assembly wherein the desired connection and/or separation of two tubes is easy.

It is a further objective of the present invention to provide a releasable tube assembly wherein the contamination of the tubes can be avoided.

To achieve these objectives, a releasable tube assembly in accordance with the present invention comprises: a male tube having a male tube body and a pair of opposing arms, in which the male tube body has an outer surface and a coupling end, and each of the arms includes: an attachment section, coupled to the outer surface of the male tube body; an intermediate angled section, extending upward from the attachment section; and a handle section, extending upward from said angled section, in which the intermediate angled section and the handle section are in non-contact with the outer surface of the male tube body; a female tube including: a female tube body having a connecting end which is tightly fitted with the coupling end of the male tube body; and a receiving chamber which connects to the connecting end of and communicates to the female tube body, in which the receiving chamber has an upper opening and two diametrically protruding hollow side wings to form a dimension which accommodates the intermediate angled sections of the opposing arms coupled to the male tube body, and the upper opening of the receiving chamber is provided with an inner flange for preventing the angled sections of the arms from leaving the receiving chamber.

The structure and objectives of the present invention will be more readily understood by those skilled in the art from the following description of the preferred embodiments taken in conjunction with the accompanying drawings.

DETAILED DESCRIPTION OF THE PREFERRED EMBODIMENT

Figure 1:
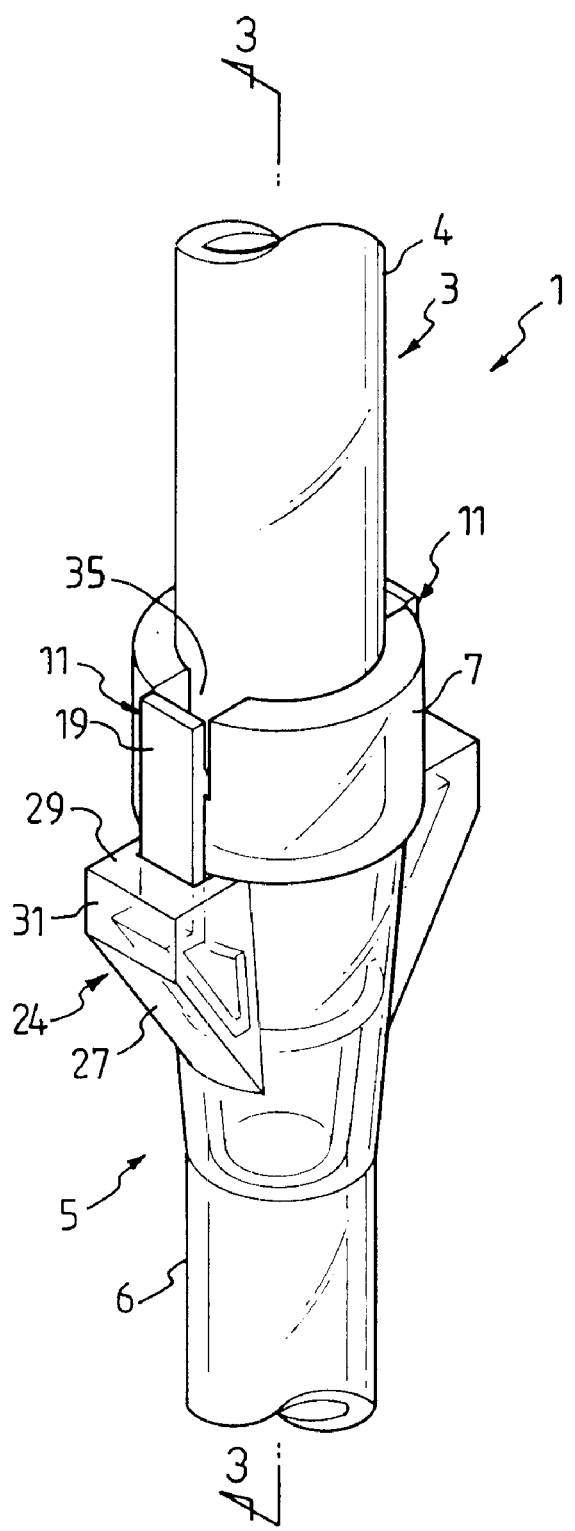
FIG. 1 is a perspective view of a releasable tube assembly in accordance with the present invention.
Figure 2:
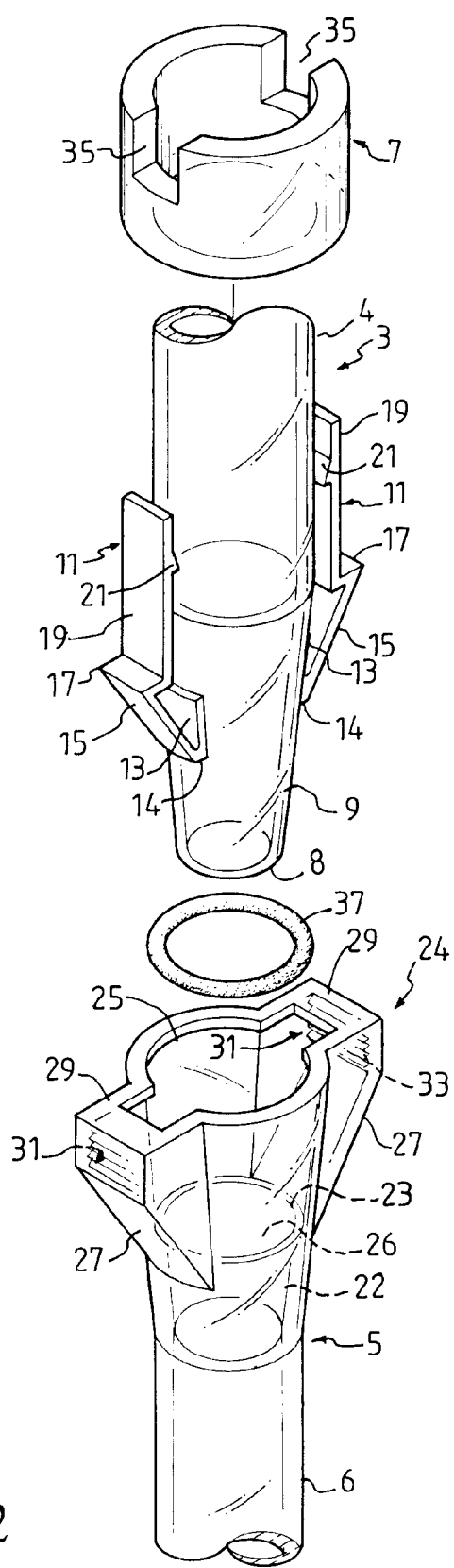
FIG. 2 is an exploded view of a releasable tube assembly in accordance with the present invention.

As shown in FIGS. 1 and 2, a releasable tube assembly 1 in accordance with the present invention comprises a male tube 3, a female tube 5 and a stop ring 7.

Figure 3:
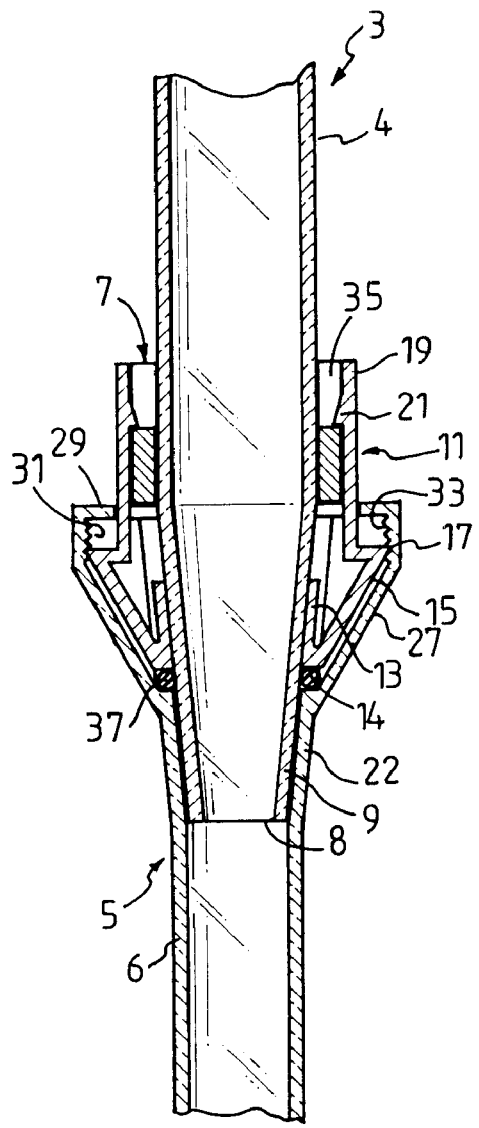
FIG. 3 is a cross sectional view taken along Line 3—3 in FIG. 1.

The male tube 3 has a male tube body 4 and a pair of opposing arms 11. The male tube body 4 has an outer surface and a coupling end 8. Each of the arms 11 is substantially a flat rectangular sheet and is preferably made of deformable material. As shown in FIGS. 2 and 3, a portion of the arm 11 is folded upward to form an attachment section 13 with a sharp edge 14 and the remaining portion is folded to form an intermediate angled section 15 with a sharp edge 17. A handle section 19 further extends upward from the angled section 15. As shown in FIG. 2, the attachment section 13 is coupled to the outer surface of the tapered section 9 of the male tube body 4. Preferably, the male tube body 4 has a gradually increasing diameter to define a first tapered section 9, which extends upward from the coupling end 8 thereof to where the attachment section 13 at each of the arms 11 is coupled. The coupling between the sections 9 and 13 is preferably made by ultrasonic welding or adhesive bonding, but can also be made by other methods. In addition, the angled section 15 and the handle section 19 are in non-contact with the outer surface of the male tube body 4 such that the two opposing handle sections 19 can be resiliently pressed and after they are released, the arms 11 will recover to their original shape without causing permanent deformation. A protrusion 21 extends from each of the handle sections 19 of the arms 11 toward the outer surface of the male tube body 4.

The female tube 5 includes a female tube body 6 and a receiving chamber 24. The female tube body 6 has a connecting end 23. Preferably, the female tube body 6 has a gradually increasing diameter at the connecting end 23 thereof to define a second tapered section 22 which tightly receives the first tapered section 9 of the male tube body 4 by interference fitting. The receiving chamber 24 connects to the connecting end 23 of and communicates to the female tube body 6.

The receiving chamber 24 is substantially defined by a hollow cylindrical body having an upper opening 25, a lower opening 26 and two diametrically protruding hollow side wings 27 to form a dimension for receiving the angled sections 15 of the arms 11 coupled to the male tube body 4. The upper opening 25 is formed for the male tube body 4 inserting thereinto and is provided with an inner flange 29. During assembling, after the handle sections 19 are pressed, the angled sections 15 are temporarily deformed. The inner flange 29 only allows the deformed angled sections 15 to pass through the upper opening 25 so as to prevent the recovered angled sections 15 of the arms 11 from leaving the receiving chamber 24, after the handle sections 19 are released. The lower opening 26 is integrally formed with the female tube body 6 and is used to communicate thereto.

As shown in FIG. 3, the cross-section of the receiving chamber 24 is substantially a trapezoid shape. Each of the side wings 27 of the receiving chamber 24 has an inner side wall 31 substantially parallel to the central axis of the female tube body 6. As shown in FIG. 3, each of the inner side walls 31 of the receiving chamber 24 has a plurality of horizontal grooves 33 formed thereon such that the sharp edge 17 of the angled section 15 of each of the arms 11 partially engaged in one of the grooves 33 when being received in the receiving chamber 24.

The stop ring 7 is in the shape of a cylindrical body having two diametrically opposite recesses 35 formed thereon and is slidably fitted over the male tube body 4, whereby the stop ring 7 can be fixed on the male tube body 4 with the protrusions 21 of arms 11 respectively received and positioned in the two recesses 35.

As shown in FIG. 3, to assemble the male tube 3 and the female tube 5, a washer 37 is preferably fitted onto the tapered section 9 of the male tube body 4 and is attached to the sharp edge 14 of the arms 11. The handle sections 19 are pressed downward toward the male tube body 4 with fingers to hold the male tube body 4 toward the upper opening 25 of the receiving chamber 24 until the deformed angled sections 15 are received by the side wings 27. At this moment, the handle sections 19 are released, and the two recovered angled sections 15 of the arms 11 remain within the two side wings 27, respectively. Further, the tapered section 9 of the male tube body 4 is fitted with the tapered section 22 of the female tube body 6 and the washer 37 is pressed between the sharp edges 14 of the arms 11 and the connecting end 23 of the female tube body 6 so as to seal the coupling end 8 of the male tube body 4 and the connecting end 23 of the female tube body 6 and prevent leakage.

To prevent the accidental pressing of the handle sections 19 and resulting disconnection, the stop ring 7 fitted onto the male tube body 4 is moved toward the coupling end 8 of the male tube body 4 and is engaged thereto, when the protrusions 21 of the arms 11 are positioned into the recesses 35 of the stop ring 7, respectively. The stop ring 7 resists against the handle sections 19 of the arms 11 from being pressed such that the sharp edges 17 of the arms 11 are respectively pushed in one of the grooves 33 and therefore the angled sections 15 are confined under the flange 29 within the receiving chamber 24. The engagement between the sharp edges 17 and the grooves 33 can prevent unintended disconnection. Further, by operating the handle sections 19, the upward and downward movements of the sharp edges 17 on the grooves 33 can adjust the tightness between the coupling end 8 of the male tube body 4 and the connecting end 23 of the female tube body 6, as well as the compression of the washer 37. In addition, since the point of connection is encased by the receiving chamber 24, contamination of the tubes can be avoided.

To separate the male tube 3 from the female tube 5, the handle sections 19 are pulled outward such that the protrusions 21 are shifted away from the recesses 35 and thus the stop ring 7 can be separated from the arms 11 of the male tube 3. The handle sections 19 are then pressed by fingers such that the sharp edges 17 leave the grooves 33 and the angled sections 15 are deformed. The angled sections 15 of the arms 11 can then be pulled away from the receiving chamber 24 through the upper opening 25 and the coupling end 8 of the male tube body 4 can be pulled out from the connecting end 23 of the female tube body 6 simultaneously.

Figure 4:
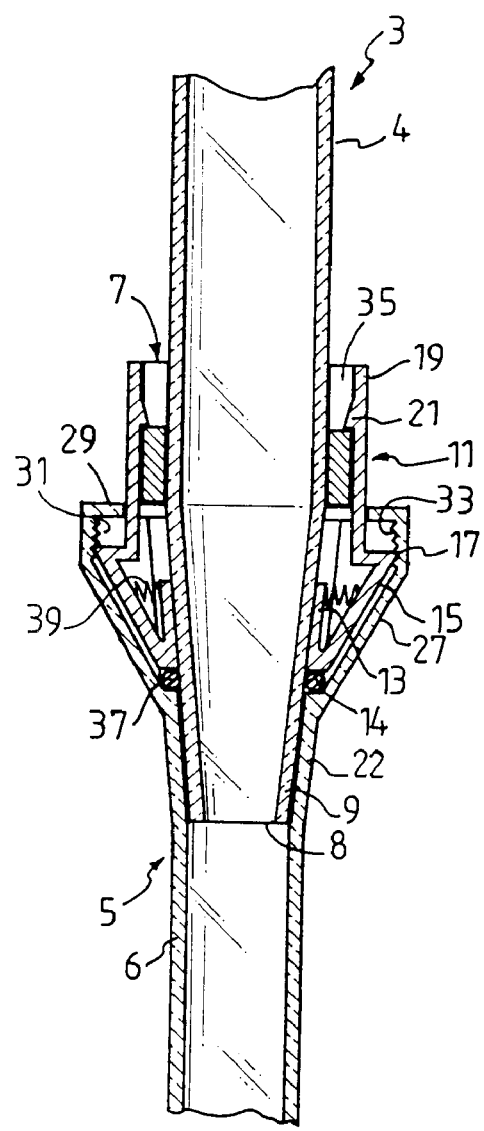
FIG. 4 is a sectional view showing the provision of a spring on both sides of the male tube body.
Figure 5:
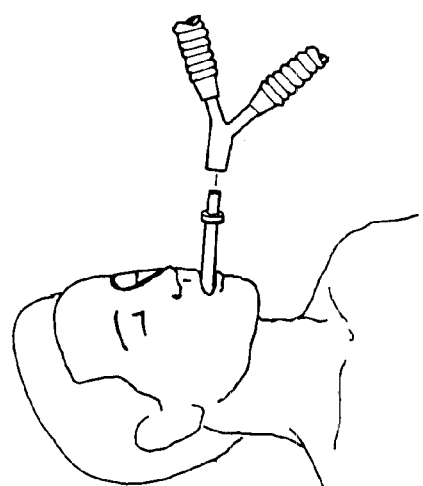
FIG. 5 is a schematic view showing the use of the conventional hub-to-hub connection.
Figure 6:
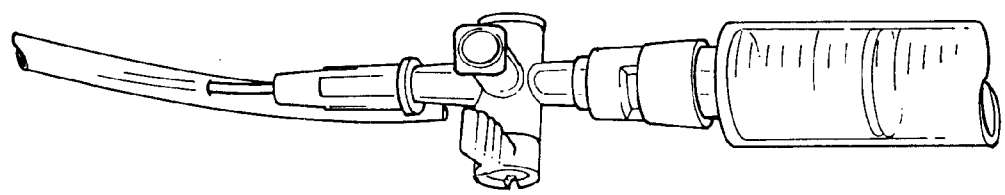
FIG. 6 is a perspective view showing the conventional male and female connection.
Figure 7:
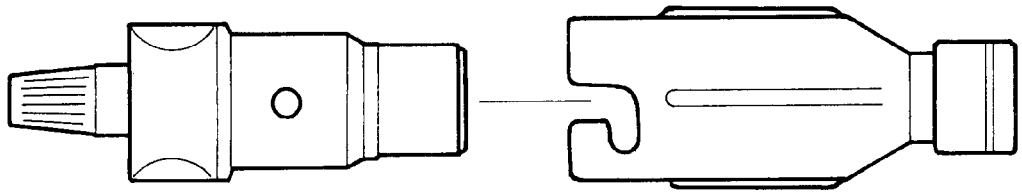
FIG. 7 is a plan view showing the conventional Saf-T-Clik connection.

Even though the present invention is primarily applied for securely connecting and sealing the ends of administration set of infusion therapy, nasogastric or nasoduodenal tubes, blood tubing set of hemodialysis, delivery tubing set of peritoneal dialysis, breathing circuit of ventilator and urinary catheters. The applications of the present invention are not limited to the above field. For example, for the connection of tubes with pressurized fluid therein, a spring 39 can be provided between the attachment section 13 and the angled section 15 so as to provide further support to ensure the sharp edge 17 can be pressed against the groove 33, as shown in FIG. 4. Furthermore, the coupling end 8 and arms 11 of the male tube 3, the receiving chamber 24 of the female tube 5, as well as the stop ring 7, can be made of transparent material such that the connection can be clearly observed.

Moreover, since the coupling end 8 of the male tube body 4 is tightly fitted within the connecting end 23 of the female tube body 6 by interference fitting, the provision of the washer 37 is not absolutely necessary. In addition, the provisions of the section 9 of the male tube body 4 and the section 22 of the female tube body 6 are not necessarily tapered but can be the same diameters as that of the male tube body 4 and the female tube body 6, as long as the section 9 can be tightly fitted within the section 22. In this alternative embodiment, the connection of the male tube body 4 and the female tube body 6 is a hub-to-hub connection.

The structure of the present invention is not limited to the above embodiments. Although the invention has been described with reference to the preferred embodiments, it will be obvious to those skilled in the art that various changes and modifications may be made without departing from the scope of the invention as recited in the claims.

What is claimed is:

1. A releasable tube assembly, comprising:
    a male tube having a male tube body and a pair of opposing arms made of deformable material, in which the male tube body has an outer surface and a coupling end, and each of the arms includes:
        an attachment section, coupled to the outer surface of the male tube body;
        an intermediate angled section, extending upward from the attachment section; and
        a handle section, extending upward from said angled section, in which the intermediate angled section and the handle section are in non-contact with the outer surface of the male tube body;
    a female tube including:
        a female tube body having a connecting end which is tightly fitted with the coupling end of the male tube body; and
        a receiving chamber which connects to the connecting end of and communicates to the female tube body, in which the receiving chamber has an upper opening and two diametrically protruding hollow side wings to form a dimension which accommodates the intermediate angled sections of the opposing arms coupled to the male tube body, and the upper opening of the receiving chamber is provided with an inner flange for preventing the angled sections of the arms from leaving the receiving chamber.

2. The releasable tube assembly according to claim 1, wherein each of the handle sections is provided with a protrusion inward extending toward the outer surface of the male tube body.

3. The releasable tube assembly according to claim 2, further comprising a stop ring which has a cylindrical body having two diametrically opposite recesses formed thereon, in which the stop ring is fitted over the male tube body with the protrusions of said arms respectively received and positioned in the two recesses.

4. The releasable tube assembly according to claim 1, wherein the receiving chamber further has a lower opening at which the connecting end of the female tube body is integrally formed.

5. The releasable tube assembly according to claim 4, further comprising a washer fitted onto the coupling end of male tube body for further sealing the coupling end of the male tube body and the connecting end of the female tube body.

6. The releasable tube assembly according to claim 1, wherein each of the side wings of the receiving chamber has an inner side wall which has a plurality of horizontal grooves formed thereon such that the angled section of each of the arms partially engages in one of the grooves when being received in the receiving chamber.

7. The releasable tube assembly according to claim 1, wherein the male tube body has a gradually increasing diameter to define a first tapered section, which extends upward from the coupling end thereof to where the attachment section at each of the arms is coupled, and wherein the female tube body has a gradually increasing. diameter at the connecting end thereof to define a second tapered section which tightly receives the first tapered section of the male tube body by interference fitting.

8. The releasable tube assembly according to claim 1, further comprises two springs, each disposed between the attachment section and the angled section of the arm.

* * * * *